United States Patent [19]
Morton

[11] Patent Number: 5,840,317
[45] Date of Patent: Nov. 24, 1998

[54] COMPOSITION COMPRISING TUMOR CELL LINES CONTAINING GD2 GANGLIOSIDE GM2 GANGLIOSIDE, M-TAA, AND EITHER M-URINARY ANTIGEN OR M-FETAL ANTIGEN

[76] Inventor: Donald L. Morton, 24752 Malibu Rd., Malibu, Calif. 90265

[21] Appl. No.: 468,029

[22] Filed: Jun. 6, 1995

Related U.S. Application Data

[60] Division of Ser. No. 961,786, Oct. 14, 1992, which is a continuation-in-part of Ser. No. 908,638, Jul. 2, 1992, abandoned, which is a continuation of Ser. No. 510,602, Apr. 18, 1990, abandoned, said Ser. No. 961,786, is a continuation-in-part of Ser. No. 431,533, Nov. 3, 1989.

[51] Int. Cl.$^6$ .................................................. A61K 39/00
[52] U.S. Cl. ...................... 424/277.1; 435/325; 435/366; 435/371; 530/828
[58] Field of Search ....................... 530/828; 424/277.1; 435/325, 366, 371

[56] References Cited

U.S. PATENT DOCUMENTS

| | | |
|---|---|---|
| 4,233,286 | 11/1980 | Soothill et al. |
| 4,557,931 | 12/1985 | Irie et al. |
| 4,562,160 | 12/1985 | Real et al. |
| 5,030,621 | 7/1991 | Bystryn |
| 5,194,384 | 3/1993 | Bystryn |
| 5,427,664 | 6/1995 | Stoev et al. |

FOREIGN PATENT DOCUMENTS

| | | | |
|---|---|---|---|
| 0 668 350 A1 | 8/1995 | European Pat. Off. | C12N 15/12 |
| 2 133 146 | 7/1984 | United Kingdom | G01N 33/54 |
| 2 188 637 | 10/1987 | United Kingdom | C12N 15/00 |

OTHER PUBLICATIONS

Gupta et al. JNCI 70(6): 993–1004 1983.
Gupta et al. JNCI 63(2): 347–56 1979.
Gupta et al. JNCI 72(1): 75–82 1984.
J. Biol. Chem 262(14): 6803–17 1987.
Melanoma Vaccines (Chapter 42) In: Cutaneous Melanoma, C.M. Balch and A.N. Houghton, Eds., publ. J.B. Lippincott Compamy PA., 542–559. 1991.
Euhus et al., "A Murine Monoclonal Antibody to a Glycoprotein Tumor Associated Antigen in Sera and Urine of Melanoma Patients," Immunology, Proceedings of AACR, Abstract, 29:393, Mar. 1988.
Euhus et al., "Demonstration and Isolation of a Glycoprotein Tumor Associated Antigen from Sera of Melanoma Patients," Biomarkers and Diagnosis, Proceedings of ASCO, Abstract, 7:44, Mar. 1988.
Euhus et al., "Effects of Melanoma Cell Vaccine on Levels of Antibody to a Tumor Associated Antigen in Melanoma Patients," In Proceedings of American Association for Cancer Research, 1987.
Euhus et al., "Measurement of a Glycoprotein Tumor Associated Antigen (TAA) Using Antibodies of Different Isotypes from a Melanoma Patient," 1988 FASEB Abstract Form.

Foshag et al., "T–Cell Cytotoxicity in Melanoma Patients Receiving Active Specific Immunotherapy (ASI) and Correlation to Clinical Outcome," Oncology, 430–431.
Foshag et al., "Specific cell mediated cytotoxicity in Melanoma Patients Receiving Melanoma Cell Vaccine (MCV) in Combination with Various Biological Response Modifiers (BRM)," Proceedings of the American Association for Cancer Research, 30:344, Mar. 1989.
Gupta and Morton, "Detection of Cancer–Associated Antigen(s) in Urine of Sarcoma Patients," Journal of Surgical Oncology, 11:65–74, 1979.
Gupta and Morton, "Immunochemical Characterization of Fetal Antigen Isolated From Spent Medium of a Human Melanoma Cell Line," JNCI, 70(6):993–1004, Jun. 1983.
Gupta and Morton, "Monoclonal Antibody–Based ELISA to Detect Glycoprotein Tumor–Associated–Antigen–Specific Immune Complexes in Cancer Patients," Journal of Clinical Laboratory Analysis, 6:329–336, 1992.
Gupta and Morton, "Studies of a Melanoma Tumor–Associated Antigen Detected in the Spent Culture Medium of a Human Melanoma Cell Line by Allogeneic Antibody. I. Purification and Development of a Radioimmunoassay," JNCI, 72(1):67–74, Jan. 1984.
Gupta et al., "Correlation of Humoral Immune Response to a Melanoma Tumor Associated Antigen with Survival of Melanoma Patients Receiving Active Specific Immunotherapy," Proceedings of the American Association for Cancer Research, ABSTRACT 30:344, Mar. 1989.
Gupta et al., "Demonstration of Two Distinct Antigens in Spent Tissue Culture Medium of a Human Malignant Melanoma Cell Line," JNCI, 63(2):347–356, Aug. 1979.
Gupta et al., "Detection of Tumor Associated Antigen in Urine of Melanoma Patients by Allogeneic Antibody," FASEB Abstract Form, Apr. 1987.
Gupta et al., "Increase in Antibody Level to a Tumor Associated Antigens in Melanoma Patients Undergoing Immunotherapy with a Tumor Cell Vaccine," Immunology and Cytokines, Proceedings of ASCO, 6:249, Mar. 1987.
Hoon et al., "A Prospective Randomized Trial of Immunomodulation with Low Dose Cyclophosphamide (CYP) in Patients Receiving Active Specific Immunotherapy with Melanoma Cell Vaccine (MCV)," Melanoma, Proceedings of ASCO, 6:212, Mar. 1987.
Hoon et al., "A Randomized Trial of Immunomodulation with Various Low Dosages of Cyclophosphamide in Patients Receiving Active Specific Immunotherapy with Melanoma Cell Vaccine," Immunology, Proceedings of AACR, 29:413, Mar. 1988.

(List continued on next page.)

Primary Examiner—Anthony C. Caputa
Attorney, Agent, or Firm—Arnold, White & Durkee

[57] ABSTRACT

A new polyvalent melanoma cell vaccine is disclosed comprised of one or more allogeneic melanoma cell lines which contain effective concentrations of melanoma associated antigens. Further disclosed are a method of stimulating an immunological response by administering the described vaccine as well as a method of prognosticating a patient.

8 Claims, No Drawings

OTHER PUBLICATIONS

Hoon et al., "Mixed Lymphocyte–Tumor Reaction and Delayed Type Hypersensitivity in Patients Receiving Specific Immunotherapy," *Immunology*, Proceedings of the American Association for Cancer Research, 31:253, Mar. 1990.

Hoon et al., "Suppressor Cell Activity in a Randomized Trial of Patients Receiving Active Specific Immunotherapy with Melanoma Cell Vaccine and Low Dosages of Cyclophosphamide," *Cancer Research*, 50:5358–5364, Sep. 1990.

Huth et al., "Relationship of Tumor–Associated Urinary Antigens to Disease Recurrence in Melanoma Patients," *Surgical Oncology*, 417–419. 1985.

Irie et al., "Antibodies to Tumor–Associated Gangliosides (GM2 and GD2): Potential for Suppression of Melanoma Recurrence," In: *Basic Mechanisms and Clinical Treatment of Tumor Metastasis*, Chapter 21, pp. 371–383, 1985.

Irie et al., "Human Monoclonal Antibody to Ganglioside GM2 for Melanoma Treatment," *The Lancet*, pp. 786–787, Apr. 1989.

Irie et al. "Humoral Immune Response to Melanoma–Associated Membrane Antigen and Fetal Brain Antigen Demonstrated by Indirect Membrane Immunofluorescence. I," *Cancer Immunol. Immunother.*, 6:33–39, 1979.

Irie et al., "Oncofetal Antigen: A Tumor–Associated Fetal Antigen Immunogenic in Man," *JNCI*, 63(2):367–373, Aug. 1979.

Kopald et al., "Complement Dependent Cytotoxicity Against Tumor Cell Lines by a Purified Baboon IgM Antibody to a Tumor Associated Antigen," *Immunology*, Proceedings of the American Association for Cancer Research, 30:346, Mar. 1989.

Morton, "Active Immunotherapy Against Cancer: Present Status," *Seminars in Oncology*, 13(2):180–185, Jun. 1986.

Morton, "Adjuvant Immunotherapy of Malignant Melanoma: Status of Clinical Trials at UCLA," *Int. J. Immunotherapy*, II(1):31–36, 1986.

Morton et al., "Active Immunotherapy of Metastatic Melanoma with Melanoma Vaccine and Immunomodulation," *Extended Abstracts*, Proceedings of the American Associated for Cancer Research, 32:492–494, Mar. 1991.

Morton et al., "Active Specific Immunotherapy of Malignant Melanoma," Chapter 13, pp. 152–161. 1989.

Morton et al., "Active Specific Immunotherapy in Malignant Melanoma," *Seminars in Surgical Oncology*, 5:420–425, 1989.

Morton et al., "Active Specific Immunotherapy with Melanoma Cell Vaccine and Immunomodulation in Patients with Metastatic Melanoma," May 19–21, 1991 ASCO Abstract of ASCO Annual Meeting.

Morton et al., "Active Specific Immunotherapy with Melanoma Cell Vaccine and Immunomodulation in Patients with Metastatic Melanoma," Abstract of Presentation at the International Conference on Biological Treatment of Melanoma and Other Cancers, New South Wales, Sep. 5–7, 1990.

Morton et al., "Adjuvant Immunotherapy of Malignant Melanoma: Results of a Randomized Trial in Patients with Lymph Node Metastases," Section VI. Melanoma, pp. 245–249, 1982.

Morton et al., "Clinical Results of a Trial of Active Specific Immunotherapy with Melanoma Cell Vaccine and Immunomodulation in Metastatic Melanoma," *Immunology*, Proceedings of the American Association for Cancer Research, 30:383, Mar. 1989.

Morton et al., "Clinical Results of a Trial of Immunotherapy with Melanoma Cell Vaccine (MCV) Plus Biological Response Modifiers," Jul. 30–Aug. 5, 1989, Abstract 7th International Congress Immunology, Berlin.

Morton et al., "Immunological Factors Which Influence Response to Immunotherapy in Malignant Melanoma," *Surgery*, 68(1):158–164, Jul. 1970.

Morton et al., "Improved Survival of Patients with Metastatic Melanoma (MM) Receiving Active Immunotherapy," *American Surgical Association*, p. 83, 1992.

Morton et al., "Long–Term Survival in Metastatic Melanoma After Active Immunotherapy with Melanoma Cell Vaccine and Immunomodulation," *Immunology*, Proceedings of the American Association for Cancer Research," 31:281, Mar. 1990.

Morton et al., "Preliminary Results of a Randomized Trial of Adjuvant Immunotherapy in Patients with Malignant Melanoma Who Have Lymph Node Metastases," *Aust. NZ, J. Surg.*, 48(1):49–52, Feb. 1978.

Morton et al., "Treatment of Malignant Melanoma by Active Specific Immunotherapy in Combination with Biological Response Modifiers," pp. 665–683, 1989.

Ravindranath and Morton, "Role of Gangliosides in Active Immunotherapy with Melanoma Vaccine," *Intern. Rev. Immunol.*, 7:303–329, 1991.

Tai et al., "Human Monoclonal Antibody Against Ganglioside $G_{D2}$: Use in Development of Enzyme–Linked Immunosorbent Assay for the Monitoring of Anti–$G_{D2}$ in Cancer Patients," *JNCI* 73(3):627–633, Sep. 1984.

Tai et al., "Immunogenicity of Melanoma–Associated Gangliosides in Cancer Patients," *Int. J. Cancer*, 35:607–612, 1985.

Tsuchida et al., "Gangliosides of Human Melanoma," *JNCI*, 78(1):45–54, Jan.1987.

Tsuchida et al., "Gangliosides of Human Melanoma," *Cancer*, 63(6):1166–1174, 1989.

Wong et al., "Augmentation of Anti–Fetal Antigen Antibody Levels in Melanoma Patients Undergoing Active Specific Immunotherapy with a Tumor Cell Vaccine," *Melanoma*, Proceedings of ASCO, 7:248, Mar. 1988.

Wong et al., "Demonstration of a Cell Surface Fetal Antigen in Circulating Immune Complexes of Melanoma Patients," 1987 Abstract 0727 Annual Meeting of American Association for Cancer Research.

Wong et al., "Documentation of the Presence of a Melanoma Tumor Associated Antigen on the Cell Surface," *Immunology and Cytokines*, Proceedings of ASCO, 6:242, Mar. 1987.

Wong et al., "Immunochemical Characterization of a Tumor–Associated Antigen Defined by a Monoclonal Antibody," *Journal of Surgical Research*, 48:539–546, 1990.

Wong et al., "Recovery of a Cell Surface Fetal Antigen From Circulating Immune Complexes of Melanoma Patients," *Cancer Immunol. Immunother*, 27:142–146, 1988.

Wong et al., "69.5 Kd glycoprotein Fetal Antigen Tumor Marker in Melanoma," Proceedings of ASCO, 7:252, Mar. 1988.

Yamamoto et al., "Generation of Lymphokine Activated Killer (LAK) Cells by Low Dose IL–2 in the Presence of Tumor Cells," Proceedings of AACR, 29:399, Mar. 1988.

Brown et al., "Structural Characterization of Human Melanoma–Associated Antigen p97 with Monoclonal Antibodies," *The Journal of Immunology*, 127(2):539–546, Aug. 1981.

Bystryn et al., "Preparation and Characterization of a Polyvalent Human Melanoma Antigen Vaccine," *Journal of Biological Response Modifiers*, 5:211–224, Jan. 1986.

Euhus et al., "Association Between Allo–Immunoreactive and Xeno–Immunoreactive Subunits of a Glycoprotein Tumor–Associated Antigen," *Cancer Immunol. Immunother*, 32:214–220, 1990.

Euhus et al., "Characterization of a 90–100 kDa Tumor–Associated Antigen in the Sera of Melanoma Patients," *Int. J. Cancer*, 45:1065–1070, Feb. 1990.

Euhus et al., "Detection of a Tumor–Associated Glycoprotein Antigen in Serum and Urine of Melanoma Patients by Murine Monoclonal Antibody (AD1–40F4) in Enzyme Immunoassay," *Journal of Clinical Laboratory Analysis*, 3:184–190, 1989.

Euhus et al., "Induction of Antibodies to a Tumor–Associated Antigen by Immunization with a Whole Melanoma Cell Vaccine," *Cancer Immunol. Immunother*, 29:247–254, 1989.

Hämmerling et al., "The Influence of Major Histocompatibility Complex Class I Antigens on Tumor Growth and Metastasis," *Biochimica et Biophysica Acta*, 907:245–259, 1987.

Hayashi et al., "Cytotoxic T Cell Lines Recognize Autologous and Allogeneic Melanomas with Shared or Cross–Reactive HLA–A," *Cancer Immunol. Immunother*, 34:419–425, 1992.

Hayashi et al., "Induction of CD4$^+$ Cytotoxic T Cells by Sensitization with Allogeneic Melanomas Bearing Shared or Cross–Reactive HLA–A$^1$," *Cellular Immunology*, 139:411–425, 1992.

Hunt et al., "Complement–Dependent Lysis of Tumor Cells By a Baboon IgM Antibody to a Tumor–Associated Antigens," *Cancer Immunol. Immunother*, 34:377–382, 1992.

Irie et al., "Melanoma, Gangliosides and Human Monoclonal Antibody," *Human Tumor Antigens and Specific Tumor Therapy*, 115–126, 1989.

Livingston et al., "Vaccines Containing Purified GM2 Ganglioside Elicit GM2 Antibodies in Melanoma Patients," *Proc. Natl. Acad. Sci. USA*, 84:2911–2915, May 1987.

Morton et al., "Prolongation of Survival in Metastatic Melanoma After Active Specific Immunotherapy With a New Polyvalent Melanoma Vaccine," *Ann. Surg.*, 216(4):463–482, Oct. 1992

Ravindranath et al., "An Epitope Common to Gangliosides O–Acetyl–$G_{D3}$ and $G_{D3}$ Recognized by Antibodies in Melanoma Patients After Active Specific Immunotherapy," *Cancer Research*, 49:3891–3897, Jul. 1989.

Rote et al., "Determination of Incidence and Partial Characterization of Tumor–Associated Antigens Found in Urine of Patients Bearing Solid Tumors", Int. Cancer 26(2):203–210 Aug. 1980.

Sidell et al., "Oncofoetal Antigen I: A Target for Immune Cytolysis of Human Cancer," *Br. J. Cancer*, 40:950–953, 1979.

Urban and Schreiber, "Tumor Antigens," *Annu. Rev. Immunol.*, 10:617–44, 1992.

Voller and Bidwell, "Enzyme Immunoassays," *Alternative Immunoassays*, Chapter 6:77–86.

Wong et al., "Demonstration of a Well–Characterized Tumor–Associated Antigen on Melanoma Cell Surface," *Journal of Surgical Oncology*, 38:147–150, 1988.

Young et al., "Production and Characterization of Mouse Monoclonal Antibodies to Human Bladder Tumor–Associated Antigens," *Cancer Research*, 45:4439–4446, Sep. 1985.

Webster's Ninth New Collegiate Dictionary, published by Merriam–Webster Inc. (see p. 881) 1991.

Cohen et al. Science 262:841–843 1993.

COMPOSITION COMPRISING TUMOR CELL LINES CONTAINING GD2 GANGLIOSIDE GM2 GANGLIOSIDE, M-TAA, AND EITHER M-URINARY ANTIGEN OR M-FETAL ANTIGEN

The present application is a division of U.S. Ser. No. 07/961,786, filed Oct. 14, 1992, which is a continuation-in-part of U.S. Ser. No. 07/908,638, filed Jul. 2, 1992, now abandoned, which is a continuation of U.S. Ser. No. 07/510,602, filed Apr. 18, 1990, now abandoned; also U.S. Ser. No. 07/961,786, filed Oct. 14, 1992, is a continuation-in-part of U.S. Ser. No. 07/431,533, filed Nov. 3, 1989.

The U.S. Government has rights in the present invention pursuant to grants CA 12582 and CA 29605 from the National Cancer Institute.

BACKGROUND OF THE INVENTION

This invention relates to polyvalent melanoma cell vaccines comprised of allogeneic melanoma cell lines which contain high concentrations of antigens which are immunogenic in melanoma patients.

The concept of using vaccines to induce specific immunity against cancer has existed since the turn of the century, when cancer therapists were first attracted by the success of vaccines in inducing active immunity against infectious diseases. Cancer vaccines differ from vaccines against infectious diseases in that they are administered as therapy after the advent of disease, rather than prophylactically before the disease develops. The theory behind vaccines for cancer and infectious diseases is, however, similar. Both seek to stimulate the patient's own immune system to fight the disease through the introduction of killed whole organisms or cells, specific subcellular antigens, and non-pathologic strains of living organisms or tumor cells. Morton, Sem Oncol 1986; 13(2):180–185.

Early attempts to induce tumor regression in cancer patients by immunizing them with their own tumors or with those from other patients were not properly evaluated; they lacked suitable controls and immunologic studies to determine whether the patients had actually been successfully immunized. However, there are well-documented instances of vaccine-induced immunity against cancer in animal models and evidence for serologic and clinical responses in man to suggest that active specific immunotherapy can be developed as a modality of treatment for cancer. Active immunotherapy became a realistic strategy after it was demonstrated that the induction of DCH reactions in certain malignant neoplasms, such as those induced by the intralesional injection of BCG (an attenuated strain of Mycobacterium) resulted in the regression and eradication of the directly injected cutaneous melanoma metastases and occasionally also in the regression of uninjected metastases. These reports rekindled interest in the century-old concept of a vaccine for cancer and revived efforts to find the crucial formulas for effective vaccine therapy.

Research efforts during the past twenty-five years have been primarily directed towards the development of more effective methods for the active specific immunotherapy of melanoma. Ann. Surg., pp 463–482(October 1992), incorporated herein by reference. The conceptual basis for this focus has been based upon the original observation that the intratumoral injection of cutaneous metastases in melanoma patients with bacillus Calmette-Guerin (BCG) resulted in systemic enhancement of active immunity, producing rising titers of anti-melanoma antibodies and regression of other uninjected metastatic cutaneous lesions. See Morton et al., Surgery 1968; 64:233–240; Morton et al., Surgery 1970; 68:158–164. Biopsy of uninjected melanoma lesions that showed clinical regression demonstrated intense lymphocytic infiltration.

Limited success was experienced with the initial attempts to reproduce these observations by active immunotherapy with the intradermal or intralymphatic injection of a randomly selected tumor cell vaccine of unknown antigenicity, which was composed of irradiated allogeneic melanoma cells mixed with BCG. Morton et al., Aust NZ J Surg 1978; 48:49–52. This tumor cell vaccine will be referred to as "TCV" or "prior melanoma vaccine." It is now known that the melanoma cell lines selected for this TCV in the early active immunotherapy trials did not express an optimum quantity of melanoma-associated antigens (MAA). At that time MAA could not be quantitated in the vaccine and it was found that only 35% of immunized patients were high responders.

Thus a need exists for an effective vaccine capable of eliciting an immune reponse in melanoma patients.

SUMMARY OF THE INVENTION

The present invention provides a new polyvalent melanoma cell vaccine which is comprised of one or more allogeneic melanoma cell lines containing high concentrations of melanoma associated antigens. These antigens are known to be immunogenic in melanoma patients. These antigens include three gangliosides, GD2, GM2 and O-aceyl GD3, and three protein antigens, M-TAA, a lipoprotein and M-fetal and M-urinary, both glycoproteins.

Further disclosed are a method of stimulating an immunological response by administering the described vaccine as well as a method of prognosticating a patient.

DETAILED DESCRIPTION OF THE INVENTION

A new vaccine is disclosed, melanoma cell vaccine, also referred here to as "MCV". This vaccine consists of three allogeneic melanoma cell lines that are known to contain effective concentrations of six melanoma associated antigens, also referred to here as "MAA". These MAAs have been demonstrated to be immunogenic in melanoma patients. "Effective concentration" refers to a concentration of antigen which will elicit an immune reponse. These MAA include three gangliosides (GD2, GM2 and O-acetyl GD3), and three protein antigens (a lipoprotein M-TAA and two glycoproteins: M-fetal antigen and M-urinary antigen). These antigens are located on the cell surface, and antibodies to them have been shown to bind with complement and kill melanoma cells in vitro. Sidell et al., Cancer Immunol Immunother 1979; 7:151–155; Irie et al., In Human Tumor Antigens and Specific Tumor Therapy 1989, pp. 115–126. Immunization of patients with MCV containing these antigens induces specific immune responses to the MAA. GD2, GM2 and O-acetyl GD3 induce IgM antibodies, but M-TAA and the other protein antigens induce both IgM and IgG antibodies. Ravindranath et al., Cancer Res 1989; 49:3891–3897; Euhus et al., Cancer Immunol Immunother 1989; 29:247–254. The presence of antibodies to those MAA in melanoma patients who were not treated with the vaccine was found to correlate with survival. This suggests that these MAA are important for the natural history of melanoma because they modulate the host protective immune responses against this disease. Jones et al., J Natl Cancer Inst 1981; 66:249–254.

A Phase II trial was undertaken to evaluate the new polyvalent MCV in patients with advanced metastatic melanoma. Patients receiving this vaccine have survived significantly longer than patients previously treated with other regimens of immunotherapy or chemotherapy. The vaccine was administered to patients for melanoma metastatic to regional skin and subcutaneous sites (AJCC Stage IIIA) as well as to distant sites (AJCC Stage IV). To evaluate the improved survival of those patients receiving the new polyvalent melanoma vaccine, a comparison was made by univariate and multivariate analysis of the prognostic factors significant for survival with similar patients from our historical database. Overall, compared to previous trials, the new vaccine was significantly more effective in eliciting specific humoral and cell-mediated immune responses. Those patients who were treated with the new polyvalent MCV and developed high levels of humoral antibody and/or cell-mediated immune responses exhibited prolonged survival compared to non-responding patients.

These results demonstrate the ability of the new polyvalent MCV to sensitize patients during the course of immunization. Overall, the humoral antibody response to melanoma associated membrane antigens and delayed cutaneous hypersensitivity to the MCV and the MLTR show that melanoma patients develop both humoral and cell-mediated immunity to MCV after 2 MCV treatments and maintain sensitization after 5 MCV treatments. Parallel in vivo assessments of DCH also show significant sensitization in the MCV-treated patients. The correlation of the DCH with the MLTR and the type of responses to the individual MCV lines indicates that the cellular immune responses were amnestic, not inflammatory, or non-specific.

This new MCV is further useful for active immunotherapy in other types of human cancer, since five of the six tumor associated antigens found in our new vaccine are also present in other types of human neoplasms. The lipoprotein antigen (180 kd) is the only one whose distribution is restricted to melanoma. Although 9-0-acetylated GD3 may be restricted to melanoma, it induces cross-reacting antibodies to GD3, which is more widely distributed in other types of human neoplasms.

The low toxicity of this vaccine justifies its use as the first treatment for recurrent melanoma prior to consideration of more toxic regimens, such as IL-2, LAK or TIL therapy or chemotherapy, whose overall long-term survival benefits have not been superior to active immunotherapy with our new polyvalent melanoma vaccine. The low toxicity of MCV also makes it reasonable to consider its use as an adjuvant in earlier Stage II and III patients who are clinically free of disease following surgery.

The vaccine of the present invention comprises whole melanoma cells containing the appropriate MAA or any fragment of the cell which contains the antigenic determinant or any protein or fragment thereof isolated from the cell containing said determinant. The proteins expressing the antigenic determinant can be isolated and the specific peptides or amino acids therein can also be identified by one skilled in the art. The invention contemplates peptides encoding the antigenic determinants. One skilled in the art would be able to modify the amino acids in the peptide without substantially altering the ability of the peptide to be recognized by the antibodies. Thus, the altered peptides may be used to identify antibodies which bind with higher or lower affinities.

The vaccine can be homogenous, for example, a single peptide, or can be composed of more than one type of peptide, each of which corresponds to a portion of the cell surface containing a different melanoma associated antigen. These MAA include, but are not limited to, GD2, GM2, O-acetyl GD3, M-TAA, M-getal antigen and M-urinary antigen. Preferably the vaccine comprises at least four of these antigens. Most preferably, the vaccine comprises all six of these MAA. Further, these peptides can be derived from different malanoma cell lines. These vaccine peptides can be of variable length so long as they can elicit an immune response.

In addition, this peptide can be attached to a carrier to further increase its immunogenicity.

Alternatively, the vaccines can comprise anti-idiotypic antibodies which are internal images of the peptides described above. Methods of making, selecting and administering such anti-idiotype vaccines are well known in the art. See, for example, Eichmann, et al., *CRC Critical Reviews in Immunology* 7:193–227(1987), which is incorporated herein by reference.

The preparation of vaccines which contain an immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thur-MDP), N-acetyl-nor-muramyl-L-alanyl-D-isoglutamine (CGP11637, referred to as nor-MDP), N-acetylmuramyl-L-alanyl-D-isoglutaminyl-L-alanine-2-(1'-2'-dipalmitoyl-sn-glycero-3 -hydroxyphosphoryloxy)-ethylamine (CGP 1983A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing a MAA resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

Both the polypeptides which react immunologically with serum containing MAA antibodies and the antibodies raised against the antigenic determinants in these polypeptides, are useful in immunoassays to detect presence of MAA antibodies, or the presence of melanoma and/or melanoma antigens, in biological samples. Design of the immunoassays is subject to a great deal of variation, and a variety of these are known in the art. For example, the immunoassay may utilize one melanomal epitope; alternatively, the immunoassay may use a combination of epitopes derived from these sources; these epitopes may be derived from the same or from different melanomal polypeptides, and may be in separate recombinant or natural polypeptides, or together in the same recombinant polypeptides. It may use, for example, a monoclonal antibody directed towards a melanomal epitope(s), a combination of monoclonal antibodies directed towards epitopes of one melanomal antigen, monoclonal antibodies directed towards epitopes of one antigen, monoclonal antibodies directed towards epitopes of different antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and prognosis and containing the appropriate labeled reagents are constructed by packaging the appropriate materials, including the polypeptides of the invention containing MAA or antibodies directed against MAA in suitable containers, along with the remaining reagents and materials required for the conduct of the assay, as well as a suitable set of assay instructions.

EXAMPLES

Materials and Methods

Review of JWCI Database to Determine Historical Survival of Advanced Stage Melanoma: The clinical records of all melanoma patients treated by the staff of the John Wayne Cancer Institute were reviewed during the 20-year period between Apr. 1, 1971 and November 1991(5575 total patients). The records of these patients were coded and entered into the JWCI computerized database developed to follow melanoma patients. Entry of prospective data for new patients seen by JWCI staff was initiated in January 1981. This information is updated about patients as they progress from one stage of disease to more advanced stages while undergoing treatment at the JWCI.

The historical review of the treatment of metastatic melanoma was based on the 1396 patients who had metastatic disease to sites other than regional lymph nodes and had been entered into the database since Apr. 1, 1971. This group consists of 602 patients who had metastases upon entering the JWCI and another 863 patients who progressed after entering the JWCI. The total patient study group of 1396 was further broken down into comparison groups stratified according to the site of first metastasis. It was observed that 121 patients recurred to a regional skin or subcutaneous site (AJCC Stage IIIA) and that the remaining 1275 recurred to a distant site (AJCC Stage IV). The distant sites were further broken down to compare survival of patients who recurred initially to the brain, liver, lung, bone, GI, skin, soft tissue or distant nodal sites.

The experience recorded in the JWCI database is unique in that the clinical leadership for the treatment of these patients has been stable over the entire twenty-year period. Thus, most patients were managed by uniform criteria of work up and therapy, which has undergone minor changes over the years. Patients with solitary metastatic sites in the skin and subcutaneous tissues were treated with intralesional BCG or human monoclonal antibody to ganglioside antigens. If BCG did not induce complete regression, patients were treated by excision or hyperthermic perfusion, as described in Morton et al., *BCG Immunotherapy of Malignant Melanoma* 1974; 180:635–643; Storm et al., *Surg Gynecol Obstet* 1979; 149:17–21; Morton et al., *Biologic Therapy of Cancer* 1991, pp. 627–642. Those with metastases to visceral sites were usually managed with chemotherapy, but some patients underwent surgical resection of metastases and immunotherapy with BCG by the tine technique (Morton et al., *BCG immunotherapy of malignant melanoma* 1974; 180:635–643; Morton, *Int J Immunother* 1986; 2(1):31–36), or with a previously developed melanoma cell vaccine. Morton et al., *Aust NZ J Surg* 1978; 48:49–52. Patients whose disease progressed while on immunotherapy were treated with systemic chemotherapy consisting of single agents: Dacarbazine (DTIC), BCNU, cisplatin or one of the combination regimens primarily consisting of BOLD (Bleomycin, vincristine, CCNU and DTIC) (Morton et al., *Cancer Treatment* 1990, pp. 500–512; Goodnight et al., *Cancer Treat Rep* 1979; 63:2005–2007), or the newer cisplatin-based regimens, such as CDDP, DTIC, BCNU, and Tamoxifen. McClay et al., *Seminars in Oncology* 1988, pp. 569–577.

Active Specific Immunotherapy

Patients: Patients with regional (AJCC Stage IIIA) or remote soft tissue or visceral metastases (AJCC Stage IV) were eligible. Patients were either NED after excisional biopsy or resection of their metastatic lesions or had objectively measurable disease (AWD) at the start of therapy. Patients with prior immuno-, chemo-, or radiotherapy were deemed ineligible until 30 days after the last therapy. Patients with brain metastases were not considered unless their metastases had been resected, or brain radiation had been completed, and they were off immunosuppressive steroid medications for treatment of brain edema for at least 30 days.

Among the 187 patients whose first metastases were regional (AJCC Stage III), 61 patients received the new MCV. Among the 1350 patients with distant metastatic sites of recurrence (AJCC Stage IV), 75 received the new polyvalent MCV, while 72 were treated with a prior tumor cell vaccine (TCV). The remaining patients in the historical control groups with regional and distant metastatic disease received treatment by a variety of methods described above.

Treatment Protocol: The active specific immunotherapy protocol involved immunization of melanoma patients with a polyvalent, irradiated whole cell MCV. The patients were stratified by stage and disease status and given in a random manner either MCV alone or MCV plus one of the biologic response modifiers (BRM), which have been shown to downregulate suppressor cell activity. These BRMs include Cimetidine (CIM; 1200 mg/d) (Smith/Kline, Pa.); Indomethacin (IND; 150 mg/d) (Lederle, N.J.); or low-dose Cyclophosphamide (CYP; 75, 150 or 300 mg/m$^2$) (Johnson/Mead, N.J.).

MCV consisted of three human melanoma cell lines M10(ATCC designation CRL-12269, deposited Jan. 23, 1997), M24 (ATCC designation CRL-12270, deposited Jan. 23, 1997) and M101(ATCC designation CRL-12271, deposited Jan. 23, 1997), which were selected from a series of melanoma cell lines after careful examination for the high expression of MAA immunogenic in melanoma patients, grown and prepared for administration as described in Hoon et al., *Cancer Res* 1990; 50:5358–5364, incorporated herein by reference. MCV was produced in large batches and analyzed for MAA antigen expression to determine variance between lots. An outside laboratory screened the MCV for viral (HIV, hepatitis), bacterial and fungal infectious organisms. Equal amounts of each line were pooled to a total of 24×10$^6$ cells in serum-free medium containing 10% dimethyl sulfoxide and cryopreserved in liquid nitrogen. Before cyropreservation, the cells were irradiated to 100 GY.

Prior to treatment, MCV was thawed and washed ×3 in phosphate buffered saline. MCV was injected intradermally in axillary and inguinal regions on a schedule of every 2 wk ×3, then monthly for 1 yr. For the first two treatments, MCV was mixed with BCG (Glaxo, England) (24×10$^6$ organisms/vial). Since 1989 we have used tice strain BCG (8×10$^6$ organisms), due to non-availability of Glaxo BCG. After one year, the immunization interval was increased to every 3 months ×4, then every 6 months. Follow-up clinical and laboratory evaluations were repeated monthly, with chest X-rays every 3 mo.

Laboratory Evaluation

To evaluate the humoral antibody and cell-mediated immune response to MCV therapy, patients were evaluated prior to and at monthly intervals following immunization. The following assays were performed:

Humoral Immune Response: The antibody response to melanoma cell surface antigens following MCV immunization was evaluated by the indirect membrane immunofluorescence (IMIF) assay, as described in Morton et al., *Surgery* 1968; 64:233–240; Jones et al., *J Natl Cancer Inst* 1981; 66:249–254. Sera were tested against the M 14 melanoma after preabsorption with matched lymphoblastoid cells autologous to the test melanoma line in order to remove antibodies to HLA antigens. Saxton et al., *Int J Cancer* 1987; 21:2999–306. M 14 expresses all of the six immunogenic MAA at moderate to high levels on its cell surface. Similar assays were run against autologous melanoma cells when available. The autologous melanoma was prepared by mincing and enzymatic digestion, as described in Chang et al., *J Clin Lab Analysis* 1:326–331(1987) and placed in short term culture for 2 to 4 days in RPMI 1640 containing 5% human umbilical cord sera prior to testing in the IMIF assay.

Delayed Cutaneous Hypersensitivity (DCH): Intradermal skin tests with MCV were performed before and during therapy. One-tenth of the pooled MCV (2.4×10$^6$ cells) was administered at a remote site on the forearm. After 48 hr, the average diameter of the induration was recorded as the DCH response. The student t-test was used to compare the absolute values of DCH from wk 0 to 4 and to 16.

General immunocompetence was evaluated by sensitization and challenge to DNCB and response to common skin test antigens such as mumps and candida. The responses to purified protein derivative (PPD) antigen to which the patient became sensitized as a result of immunization with BCG in the vaccine served as additional controls.

Mixed Lymphocyte Tumor Cell Reaction (MLTR): MLTR was used to evaluate the in vitro response to immunization. Forty patients were selected on the basis of their treatment (MCV alone=10, plus CIM=11, plus IND=10, plus CYP=9) and the availability of peripheral blood lymphocytes (PBL) serial bleeds, without knowledge of their clinical condition. PBL from wk 0, 4 and 16 were isolated and cryopreserved. Assays were performed on cryopreserved lymphocytes to ensure reproducibility. Serial bleed PBL were simultaneously thawed, washed, and resuspended in culture medium [RPMI 1640 with 10% human AB serum (heat-inactivated) (Irvine Scientific, Calif.)].

Each melanoma cell line in the MCV was prepared analogous to the procedure for the vaccine production. PBL from wk 0, 4, and 16 were stimulated at a 5:1 ratio to each of the MCV lines (M10, M24, and M101). These co-cultures were performed in triplicate in 96-well microplates with culture medium supplemented with recombinant interleukin-2 20 U/ml (Amgen, Calif.) to a total volume of 200 $\mu$l. They were then incubated for 6 days at 37° C. Respective control cultures of PBL were grown in medium alone and with phytohemagglutinin (PHA) (Wellcome, N.J.) at a suboptimal concentration of 0.1 $\mu$g/ml. During the last 18 hours, the cells were pulsed with [3H]-thymidine (New England Nuclear, Mass.) and harvested. Data were analyzed for each patient as counts per minute (CPM) for each triplicate (SD<15%) at each time point. The student t-test was used to compare data from wk 0 to wk 4 and to wk 16 for each patient and for the overall study group using mean CPM. Each patient served as his/her own control.

Autologous MLTR: Autologous melanoma cells were established from patient biopsy specimens, as described above. These were obtained prior to therapy and, when available, were assessed with the MCV lines in the MLTR.

Analysis of tumor infiltrating lymphocytes (TIL) in melanoma biopsy specimens: Tumor-infiltrating lymphocytes (TIL) have been found in melanoma lesions and are strongly implicated as playing a major role in inducing tumor regression following adoptive immunotherapy. In this study, TIL was evaluated in melanoma lesions surgically removed from patients prior to MCV treatment and compared them by immunohistopathology and flow cytometry to TIL in melanoma lesions removed post-MCV treatment from those patients with evaluable lesions at the start of immunotherapy. The immunohistology and histopathological examinations were carried out by observers blinded to whether the specimens were obtained pre- or post-MCV immunotherapy.

To evaluate lymphocyte subsets, tumor specimens were made into single cell suspensions by mincing and enzyme treatment. The single cell suspensions were then stained with monoclonal antibodies CD3(T cell), CD4(T helper), CD8(T cytotoxic/suppressor), CD19(Pan B), CD25 (IL-2 receptor, TAC), and CD56(NK)(Becton Dickinson, Mountain View, Calif.) specific to individual lymphocyte subsets. The specific binding of CD marker antibodies to cell-surface antigens was then analyzed by flow cytometry using FACscan (Becton Dickinson, Calif.).

Statistical Methods: Estimated survival rates were obtained by the non-parametric Kaplan-Meier method. Kaplan et al., *J Am Stat Assoc* 1958; 53:457. The log-rank test was used to determine the differences in survival of patients from subgroups defined by different levels of risk factors. This method of univariate analysis is useful when all variables are categorized into subgroups that are maximally separated in terms of survival rates. For example, when the location of the metastatic site is examined, if the survival rate of patients with skin metastases is not statistically different from that of patients with GI metastases, but is statistically different from that of patients with lung metastases, the first two groups are combined and compared with the third. This technique was used in part to define categories for the risk factors related to sites of first metastasis. A more general rank test and the log-rank test was used to test for multivariate associations of the risk factors. A discussion of these tests can be found in Kalbfleisch and Prentice Kalbfleisch JD, Prentice RL: The Statistical Analysis of Failure Time Data. New York, Wiley & Sons, 1980. The multi-variate results were confirmed by using the Cox proportional hazards regression model. Cox, *Stat Soc* 1972; 34:187. The statistical package of SAS procedures LIFETEST and PHGLM SAS Institute: SUGI Supplemental Library User's Guide. Cary, N.C., SAS Institute, 1986 were used in the univariate and multivariate analysis.

Survival time was defined as the time a patient remained alive after the documented date of metastatic disease to either a regional site (AJCC Stage IIIA), in regards to skin and soft tissue metastasis, or a distant site (AJCC Stage IV). The distant sites were further characterized by the site of the metastasis.

Results

Evaluation of the Immune Response to Active Immunotherapy with MCV: Most patients demonstrated evidence of a prompt response. A specific anti-melanoma immune response was often induced within 2 wk, reaching a peak response in 4 to 8 wk, and gradually declining in most patients to a level significantly above preimmunization levels. As shown below, it is clear that the extent to which the humoral and cell-mediated immune responses are enhanced in these patients correlates with a favorable outcome.

Humoral Immune Response: It was found that IgM antibody to cell surface antigens correlated best with survival. No significant correlation with IgG antibody to melanoma cell surface antigens was found. The induction of IgM antibodies to membrane-associated melanoma antigens found on the M 14 melanoma was observed in 62% of patients immunized with the new MCV. This was significantly improved over the 35% response to the previous TCV. Morton et al., *Aust NZ J Surg* 1978; 48:49–52; Jones et al., *J Natl Cancer Inst* 1981; 66:249–254. Autologous melanoma cells were available for use as targets in tests of 26 patients receiving the MCV. It was found that 4/26 patients had pre-existing antibody to autologous melanoma cells at titers of <1:10 prior to active immunotherapy with the MCV. Following immunotherapy, 17/26 patients exhibited antibodies to membrane-associated autologous melanoma antigens to a mean titer of 1:29. This was similar to the observed response to membrane antigens on the allogeneic (M-14) melanoma cells. It should be noted that M 14 melanoma is not a component of the melanoma vaccine, but that parallel rises in antibody to autologous melanoma cells and M 14 were observed in most patients. These data clearly indicate the sharing of common MAA among the MCV and the autologous melanoma cells, thus confirming previous observations with the humoral response to allogeneic MCV. Jones et al., *J Natl Cancer Inst* 1981; 66:249–254.

High levels of anti-melanoma antibodies with membrane immunofluorescence indices of >50% were associated with significant (p=<0.01) improvement in survival, as previously reported with the prior TCV. Jones et al., *J Natl Cancer Inst* 1981; 66:249–254. It was observed that almost a threefold increase in five-year survival (9.6% to 26.8%) and twofold increase in median survival from 16 to 30 months among the high responders.

Delayed Cutaneous Hypersensitivity: Most patients were judged generally immunocompetent by their response to PPD, DNCB, and/or common skin test antigens.

When all patients were stratified by their maximum skin test reactions to MCV, there was a highly significant (p=0.0066) correlation between survival following treatment and a DCH reaction >10 mm during the first 12 week after initial MCV therapy. The median survival was 30 months for those >10.0 mm and only 17 months for those <10.0 mm. Five-year survival increased from 10% to 27.7%.

Mixed Lymphocyte Tumor Reactions (MLTR): To evaluate the cellular immune response of in vivo stimulation with MCV, MLTR were performed with the individual MCV lines. Overall, MLTR with M10, M24, and M101 were significantly increased at week 4 compared to week 0, and the level of response to each MCV line remained significant at week 16. The patterns and magnitude of the patients' responses were similar in MLTR performed without the presence of IL-2. There is a similarity between the in vivo DCH response to the MCV and the in vitro MLTR in the 40 patients for whom there was data on both cell-mediated assays.

Of the 40 patients, 82% showed significantly (p<0.05) enhanced stimulation to one or more of the MCV lines at either week 4 or 16 compared to week 0. Of these, 91% had evidence of sensitization to $\geq 2$ MCV lines. More patients showed sensitization at week 4 to M24 and M101 (73% and 75%, respectively) than to M10(38%), and more maintained sensitization at week 16 to M24 and M101(51% and 62%, respectively) than to M10(35%).

The proliferation of PBL in medium alone, and with PHA, was assessed at week 0, 4 and 16. Overall, at each time point, PBL response was significantly (p<0.05) greater with PHA than in medium alone. More importantly, comparisons from week 0 to 4 and 16 showed no significant differences, either with medium alone or PHA. These and additional controls, along with the variable responses to the MCV lines, indicated that the MLTR responses were not the result of non-specific responses to cryopreservation, culture medium, serum antigens in the AB serum, or preparation procedures, although the nature of the antigens to which the lymphocytes in the MLTR react is complex and probably involves MHC Class I or II antigens, as well as specific MAA. There was a clear-cut correlation between response in MLTR and survival as discussed below. Furthermore, the parallel responses of autologous melanoma cells indicate that antigens other than MHC are involved in the MLTR assays.

Autologous MLTR: To determine whether patients become sensitized to their own melanomas as well as to the allogeneic MCV cells during MCV immunotherapy, autologous melanoma MLTR were performed in parallel with MLTR against MCV vaccine lines. Two representative patients were chosen who demonstrated significant sensitization toward their own melanoma at week 4 and 16 compared to week 0. One patient had evidence of pre-treatment sensitization to his own melanoma, which was significantly augmented during MCV therapy. Thus, immunization with this allogeneic melanoma vaccine clearly enhanced response to the autologous melanoma, confirming the observations of cross-reacting antigens, seen by humoral antibody to membrane-associated antigens.

MLTR Correlation with Clinical Data: Of the 40 patients, 37 were clinically NED at the start of treatment; 28 were Stage III; and 9 were Stage IV. At the time of analysis, 25/37(68%) were alive, with a mean follow up of 26 months (range 14–50 month). Of these, 16 remained NED, 5 had had surgical resection of a recurrence and were REC-NED, and 4 had recurrent disease with progression and were AWD. Twelve patients, 10 Stage III and 2 Stage IV, expired (mean of 19 month, range 8–32 month) from time of treatment.

Disease-free and overall survival for the 37 patients who began treatment NED were correlated with the individual patient's response to MCV by MLTR. Week 16 was selected as the evaluation point based upon the number of vaccinations (N=5).

The disease-free survival at 2 yrs was 53%±10% SEM for patients responding to one or more MCV lines in the LTR, compared to 20%±13% SEM for patients who showed no response; the difference between the 2 groups approached significance (p=0.055). In the responding patients, the median time to recurrence was >29 mo nth, compared to 12 months in the non-responders. The overall survival at 2 years was 78%±9% SEM for the responding patients, compared to 50%±16% SEM for the non-responders. Again, the difference between the 2 groups approached significance (p=0.065). The median survival was >36 months in the responders, compared to 20 months in the non-responders.

Analysis of TIL in Patients Receiving Active Immunotherapy: A detailed analysis of the histopathology of melanoma biopsy specimens of patients receiving active immunotherapy revealed an increase in intratumoral lymphocytes infiltrating the melanoma cells. This phenomenon is illustrated by hematoxylin and eosin staining of a biopsy of a post-MCV pulmonary metastases. Pan T staining indicated that the lymphocytes in this specimen are primarily T cells. Little staining was observed with a Pan B stain. In addition to the findings regarding TILs, there was an increase observed in the post-immunization biopsies of both single cell necrosis (defined as isolated necrotic cells surrounded by lymphocytes) and confluent necrosis indicated by sheets of necrotic cells.

An interesting observation in the patients receiving MCV was the appearance of peripheral lymphoid aggregates surrounding melanoma metastases in the subcutaneous tissues. These aggregates contained both T and B cells, which appeared to be organized into lymphoid follicles.

To confirm further findings regarding changes in post-immunization specimen histopathology, a study of pre- and post-immunization biopsies was undertaken to evaluate changes in lymphocyte subsets of the TILs by flow cytometry using FACscan. Analysis was made of 5 pre-MCV biopsies and 9 post-MCV melanoma biopsies for specific TIL subsets. A comparison of pre-MCV versus post-MCV biopsies showed an increase in the CD4+/CD8+ ratio of the post-immunization biopsies from a mean of 0.93 to 2.13. Although they were not statistically significant (p=0.10), the results show a strong trend in the reduction of CD8+ T cells (most likely-suppressor T cells) in post-MCV biopsies. In one of the pre-MCV treated specimens the CD4+/CD8+ ratio was unusually high. In the same patient's post-MCV treated specimen, this ratio was further enhanced. This patient's post-MCV specimen also had a high level of activated TILs with IL-2 receptors (CD25+). Similar changes were noted in the pre- and post-MCV specimens of another patient. In the other post-MCV specimens there was an overall statistically significant enhancement of CD25+ (p<0.05) and CD56+ (p<0.04) cells. The presence of a higher level of CD25+ cells in the post-MCV specimens indicate an increased level of lymphocyte activation, which is consistent with the findings of immunohistopathology. Although it would have been preferable to have matched specimens for comparison of pre- and post-MCV in the same patient, this was not possible, because both specimens for flow cytometric analysis were not available except for the two patients discussed above. Data from these two patients and the paired specimens from many more patients that were available for histopathology study confirmed the changes noted in random flow cytometry studies of pre- and post-immunization biopsies.

The overall findings indicate that active specific immunotherapy with our new polyvalent allogeneic melanoma vaccine appears to be followed by enhanced activation of specific lymphocyte subsets within the melanoma specimen. These lymphocytes appear to migrate to the site of melanoma metastases and may be responsible for the complete and partial melanoma regressions, as well as, the delayed progression observed following active immunotherapy.

Univariate and Multivariate Analysis of Prognostic Factors: Patients with AJCC Stage IIIA regional soft tissue metastases survived significantly (p=0.0001) longer than those with distant metastases (AJCC Stage IV). Therefore, it was necessary to analyze those two stages separately when comparing survival in patients being immunized with the new MCV. Of the factors analyzed by univariate and multivariate analysis, only two factors were significant for prognosis in Stage IV melanoma. One was the site of metastasis, with the skin, subcutaneous, GI and nodal sites being the most favorable; lung and bone being intermediate; and the liver and brain being the least favorable. The other major prognostic factor that was highly significant was whether or not the patients received immunotherapy with the new MCV. Those patients who received the new MCV survived significantly longer than those who were treated by other means. Unlike Balch, (*J Clin Oncol* 1982; 1:126), we did not find the remission duration or number of metastatic sites to be of prognostic significance by multivariate analysis. However, the number of metastatic sites were closely matched in the MCV and historical control groups.

Analysis of the Influence of the Chronological Time Interval of Treatment on the Survival of Patients with Metastatic Melanoma: Because the chronological time interval of treatment could have been an important factor in the survival of the historical control patients, the patients receiving other treatments were divided into three groups of 6- or 7-year periods to determine whether there had been an improvement in survival of patients in the other treatment groups that might explain the improved survival observed in our most recent patients receiving the new MCV. A comparison of survival during various time intervals for patients with AJCC Stage IIIA and AJCC Stage IV disease who received other treatments revealed that there has been no improvement in the survival of patients with metastatic melanoma who received non-MCV therapy and were seen by the staff of the John Wayne Cancer Institute during the past twenty years. This is not surprising since the standards of care for patients with metastatic melanoma have remained very much the same during the past twenty years and there has been little improvement in survival observed with different chemotherapy regimens. Thus, the improved survival of patients receiving the new melanoma cell vaccine cannot be related to chronological differences in the time frame in which these patients were treated.

Comparison of Overall Survival Between Active Immunotherapy and Historical Control Groups: There was a highly significant improvement in the survival of patients receiving active immunotherapy with the new polyvalent MCV in both AJCC Stage IIIA and Stage IV disease. The median survival of Stage IV was increased threefold from 7.5 to 23.1 months and five-year survival was increased fourfold from 6% to 26%.

However, the distribution of patients receiving other therapy differs from that of those receiving immunotherapy: the "other" patients were slightly more likely than patients receiving the new MCV to have brain (9%) and liver (7%) metastases and less likely to have skin or subcutaneous metastases (18%), whereas patients receiving the old TCV showed a distribution of metastatic sites that was quite similar (within 8 to 12%) to that of patients receiving the new vaccine. It is unlikely that such small differences in distribution of metastases could be responsible for such large differences in survival between the two groups of patients with Stage IV disease.

Multivariate analysis took into account the differences in risk factors in comparing the two survival curves, however, it was thought to be important to exclude the possibility of bias due to a more favorable pattern of metastatic sites being present in the patients receiving immunotherapy with the new vaccine. Therefore, the two groups were directly compared for three metastatic sites of patients treated by "other" treatment versus those of patients receiving the new MCV. A comparison was made of the metastatic sites of the lung; skin, subcutaneous, and nodal sites; and liver and brain. Again, it was found that those patients receiving the new vaccine survived significantly longer than those patients treated by other methods. Furthermore, patients receiving the new MCV demonstrated a highly significant improved survival compared to those receiving the old TCV.

Finally, the possibility of a bias was investigated due to the fact that the patients who had received the new melanoma vaccine had been more recently entered into the trial. Since many of them were still alive, their data was censored. This may have created a bias when compared to the other data sets where more of the patients had died. To investigate this possible bias, the survival rates of the two groups of patients was compared focusing only on those patients who had expired of melanoma in the subsets of patients with lung metastases or skin and subcutaneous metastases. Again, there was a highly significant improvement in survival for both sites in those patients who had received immunotherapy with the new vaccine as compared to the patients treated by other therapies. Thus, it is clear that censoring cannot explain the apparent increased survival in those patients receiving the polyvalent MCV.

Clinical Results in Patients with Evaluable Disease at the Time of Initiation of Immunotherapy: A total of 40 Stage IV patients entered the study with evaluable metastatic disease and were observed for 12 wk after the initiation of immunotherapy. Regressions were observed in 9 of the 42 patients, an objective regression rate of 22%. Three complete responses and six partial responses were observed. The majority of patients exhibited progressive disease that required the institution of other therapies, primarily chemotherapy. However, stabilization in growth of metastasis was sometimes observed, and in some patients, such as those with pulmonary metastasis, the growth rates before and after the beginning of immunotherapy could be objectively measured based upon the tumor doubling time. In some cases, there was a clear reduction in the growth rate of the metastatic disease.

It was not unusual for patients to observe tenderness and swelling, sometimes accompanied by erythema, pain or itching, at the sites of melanoma metastases beginning 2 to 4 days after repeated booster immunizations. One patient exhibited bruising at sites of subcutaneous metastases, followed by complete regression of that particular subcutaneous metastases.

Case number one is a fifty-three-year-old man whose primary melanoma was behind the ear. The primary was treated by wide excision and a radical neck dissection. No lymph nodes were involved, and the patient remained well for 4 years. After 4 years, recurrent in-transit disease developed surrounding the primary despite adjuvant DTIC and BCG. The disease on the head and neck was treated with electron beam radiation with some response, followed by further progression. At the time the immunotherapy was initiated (Jan 6, 1986), extensive, multiple metastases were present over the right cheek, ear, and scalp, posterior to the ear as well as extending to both sides of the neck. Approximately 12 weeks after the initiation of immunotherapy with the polyvalent MCV, using low dose cyclophosphamide 300 mg/$M^2$ as an immunomodulator, certain of the patient's metastatic lesions showed some flattening and a reduction in size. During the following 10 months, a complete regression of all metastases occurred concomitantly with continuation of MCV immunotherapy. The anti-melanoma antibody titers to membrane-associated MAA began to rise after 4 weeks.

Brain metastases were suspected after a seizure, and the MRI revealed a mass lesion, but no melanoma cells were found in specimens following craniotomy and resection, suggesting the immunotherapy had caused regression of the brain metastases. The patient remained in complete remission for an additional year, at the end of which a small recurrent nodule was noted on the ear. Treatment with intralesional injections of human monoclonal antibody produced complete regression of the nodule. The patient was continued on melanoma vaccine and remained well until 4 ½ years after the onset of the immunotherapy, when he again experienced seizures. Workup then revealed meningeal spread of his melanoma. After shunt placement for increased intracranial pressure, he was treated with chemotherapy using a cisplatin-based regimen, but the patient expired 4 months later.

Case number two is a 60-year-old woman with a Clark's level IV melanoma of the thigh, which was treated by a wide excision and a radical inguinal lymphadenectomy. Eighteen months later, she developed multiple satellite metastases around the site of the primary. These were treated with radiation and local hyperthermia, which resulted in a burn at the site of the hyperthermia. Her melanoma continued to progress with multiple metastatic lesions involving the entire thigh and extending above the inguinal ligament. The patient was seen in the John Wayne Cancer Clinic in April of 1989, at which time a biopsy of cutaneous metastases revealed active melanoma. Immunotherapy with the polyvalent MCV was initiated. The disease continued to progress until 8 weeks after the initiation of the new vaccine, when it appeared to stabilize. From 12 to 16 weeks, there was clear evidence of regression in the cutaneous in-transit metastases, and over the next 3 months her disease underwent a complete regression. The actively growing melanoma nodules were replaced by flattened pigmented areas which have gradually faded. Biopsy of these pigmented lesions revealed no visible melanoma cells, only pigment in macrophages. The patient has been maintained on the new MCV every 2 mo. She is now 4 years 4 months since the initial recurrence and 4 years since the initiation of immunotherapy. A recent workup, including full-body CAT scans, showed no evidence of recurrence at any site.

Case number three is a forty-year-old woman with ocular melanoma who presented with multiple liver metastases visible on a CAT scan. Since it was not known whether her ocular melanoma shared cross-reacting antigens with cutaneous melanoma, an exploratory laparotomy was carried out and one of the metastases was resected in the left lobe of the liver to obtain tissue for antigenic typing. It was found that her ocular melanoma shared most of the antigens with cutaneous melanoma. CTL generated by stimulation with the patient's melanoma killed HLA-A-matched allogeneic cutaneous melanoma. Active specific immunotherapy using the polyvalent MCV was proceeded with. A repeat CAT scan 3 months after the initiation of immunotherapy revealed a 75% regression of the metastatic disease in the right lobe of the liver. The response was maintained for another 3 months, but then the disease began to progress, and chemotherapy with a cisplatin-based regimen was instituted. The patient expired 15 months after the initiation of immunotherapy.

Toxicity:

Galaxo and Tice Strain BCG at dosages of 8 million and 4 million organisms admixed with the MCV on the first and second treatment cycles respectively cause local erythema, induration and ulceration at the sites of intradermal administration. This is most notable in tuberculin-positive patients for whom the above dosages are diminished by half. Low grade fever is noted by about 35% of patients, usually within the first 72 hours following treatment with BCG, sometimes accompanied by myalgia and arthralgia. Fewer than 10% of patients report myalgia, arthralgia, chills or rigors. These symptoms, when they occur, generally last less than 48 hours and respond to aspirin.

Local ulcerations generally peak by about week 4 of treatment and heal progressively over approximately 8 weeks. The remaining scars are generally modest in degree and tend to fade slowly over 8–10 months. In general, both local and systemic toxicity is less than previously observed with intralesional BCG. Hoon et al., *Proc Am Assoc Cancer Res* 1991; 32:236, no. 1400.

MCV, when administered alone, is very well tolerated, with virtually no significant toxicity when administered up to 5 years at 3-month intervals. Mild erythema and itching are noted in the treatment sites by a majority of patients. This is transient, lasting only 2–3 days. About 15% of patients report low grade fever of <99° F. for 12 to 24 hr. A similar proportion of patients report mild fatigue on the day or two following treatment with MCV alone. Myalgia and arthralgia are rarely reported.

Furthermore, there is definitive in vitro data and conclusive in vivo data to indicate that a higher degree of cell mediated and humoral antibody immunity is induced by the allogeneic vaccine if there are shared MHC class I HLA antigens between the vaccine and the patient being immunized. See Hayashi et al., *Cancer Immunol. Immunother* 1992, 34:419–423; Berd et al., *Cancer Res* 1986, 46:2572–2577.

While the present invention has been described by way of specific examples, the scope of the invention is not limited as additional embodiments will be apparent to those of skill in the art of the present disclosure.

I claim:

1. A composition comprising viable cells of one or more tumor cell lines, which cell line or lines provide to a composition an antigenically effective amount of each of GD2 ganglioside, GM2 ganglioside, M-TAA, and either M-fetal antigen or M-urinary antigen, the antigens being included in the composition in amounts effective to elicit an antibody response against said antigens, the composition being suitable for injection to an animal and said one or more tumor cell lines rendered incapable of proliferation in vivo.

2. The composition of claim 1, wherein the cell line or lines provide to the composition an antigenically effective amount of GD2 ganglioside, GM2 ganglioside, M-TAA, M-fetal antigen and M-urinary antigen.

3. A pharmaceutically acceptable composition comprising one or more cell lines selected from the group consisting of cell line M10(ATCC CRL-12269), M24(ATCC CRL-12270), and M101(ATCC CRL-12271), the composition comprising a pharmaceutically acceptable excipient or diluent, wherein said one or more cell lines are rendered incapable of proliferation in vivo.

4. The composition of claim 3, wherein the selected cell line is M10(ATCC CRL-12269).

5. The composition of claim 3, wherein the selected cell line is M24(ATCC CRL-12270).

6. The composition of claim 3, wherein the selected cell line is M10(ATCC CRL-12271).

7. The composition of claim 3, wherein the composition includes all three cell lines.

8. The composition of claim 3, wherein the one or more cell lines have been rendered incapable of proliferation by irradiation.

* * * * *

UNITED STATES PATENT AND TRADEMARK OFFICE
CERTIFICATE OF CORRECTION

PATENT NO.  : 5,840,317
DATED       : November 24, 1998
INVENTOR(S) : Donald L. Morton It is certified that error appears in the above-identified patent and that said Letters Patent is hereby corrected as shown below:

On the title page: Item [54] and Column 1, line 3, insert a comma between 'GANGLIOSIDE' and 'GM2' so that the title reads as follows: *"COMPOSITION COMPRISING TUMOR CELL LINES CONTAINING GD2 GANGLIOSIDE, GM2 GANGLIOSIDE, M-TAA, AND EITHER M-URINARY ANTIGEN OR M-FETAL ANTIGEN"*.

In claim 6, column 16, line 40, delete "M10", and insert the following therefor: -- M101 --.

Signed and Sealed this

Thirtieth Day of March, 1999

Attest:

Q. TODD DICKINSON

*Attesting Officer*

*Acting Commissioner of Patents and Trademarks*